United States Patent
Yuan et al.

(10) Patent No.: US 12,029,620 B2
(45) Date of Patent: Jul. 9, 2024

(54) PEELING TYPE LASER TOOTH PREPARING METHOD, APPARATUS AND DEVICE, AND MEDIUM

(71) Applicant: Beijing University School of Stomatology, Beijing (CN)

(72) Inventors: Fusong Yuan, Beijing (CN); Peijun Lv, Beijing (CN)

(73) Assignee: Beijing University School of Stomatology, Beijing (CN)

( * ) Notice: Subject to any disclaimer, the term of this patent is extended or adjusted under 35 U.S.C. 154(b) by 1036 days.

(21) Appl. No.: 16/960,830

(22) PCT Filed: Apr. 3, 2018

(86) PCT No.: PCT/CN2018/081698
§ 371 (c)(1),
(2) Date: Jul. 8, 2020

(87) PCT Pub. No.: WO2019/183992
PCT Pub. Date: Oct. 3, 2019

(65) Prior Publication Data
US 2020/0352678 A1 Nov. 12, 2020

(30) Foreign Application Priority Data
Mar. 27, 2018 (CN) .......... 201810257517.7

(51) Int. Cl.
*G01N 33/48* (2006.01)
*A61C 1/00* (2006.01)
(Continued)

(52) U.S. Cl.
CPC .......... *A61C 1/0046* (2013.01); *A61C 1/0007* (2013.01); *B23K 26/38* (2013.01);
(Continued)

(58) Field of Classification Search
CPC .. A61C 1/0046; B23K 26/38; G05B 19/4155; G05B 2219/45041; G05B 2219/45167; G06T 17/00; G06T 19/00
See application file for complete search history.

(56) References Cited

U.S. PATENT DOCUMENTS

2006/0183082 A1 8/2006 Quadling et al.
2010/0173266 A1 7/2010 Lu et al.

FOREIGN PATENT DOCUMENTS

CN 102486641 A 6/2012
CN 103886145 A 6/2014
(Continued)

OTHER PUBLICATIONS

Li et al. A fast segmentation method for STL teeth model. 2007 IEEE/ICME International Conference on Complex Medical Engineering, pp. 163-166. (Year: 2007).*

*Primary Examiner* — Russell S Negin
(74) *Attorney, Agent, or Firm* — Bookoff McAndrews PLLC

(57) ABSTRACT

A peeling type laser tooth preparing method, apparatus and device, and a medium. Method comprises: acquiring a first STL model of a target tooth and a second STL model of a tooth preparation of the target tooth; generating a conical peeling curved-surface STL model, in a manner of taking a three-dimensional curve of a peripheral edge contour of a shoulder in the second STL model as a bottom edge; carrying out Boolean calculation on the peeling curved-surface STL model and the first STL model to obtain a third STL model; carrying out Boolean calculation on the second STL model and the third STL model to obtain a fourth STL model required to be removed; generating a multilayer laser cutting path according to the fourth STL model, controlling a laser tooth preparing device to perform the tooth preparing
(Continued)

process of the target tooth according to the multilayer laser cutting path.

12 Claims, 17 Drawing Sheets

(51) Int. Cl.
| | |
|---|---|
| *B23K 26/38* | (2014.01) |
| *G01N 33/50* | (2006.01) |
| *G05B 19/4155* | (2006.01) |
| *G06T 17/00* | (2006.01) |
| *G06T 19/00* | (2011.01) |
| *G16H 20/40* | (2018.01) |
| *G16H 40/63* | (2018.01) |
| *G16H 50/20* | (2018.01) |
| *G16H 50/50* | (2018.01) |
| *G16H 70/20* | (2018.01) |

(52) U.S. Cl.
CPC .......... *G05B 19/4155* (2013.01); *G06T 17/00* (2013.01); *G06T 19/00* (2013.01); *G16H 20/40* (2018.01); *G16H 40/63* (2018.01); *G16H 50/20* (2018.01); *G16H 50/50* (2018.01); *G16H 70/20* (2018.01); *G05B 2219/45041* (2013.01); *G05B 2219/45167* (2013.01); *G06T 2219/008* (2013.01)

(56) References Cited

FOREIGN PATENT DOCUMENTS

| | | |
|---|---|---|
| CN | 104546151 A | 4/2015 |
| CN | 104699865 A | 6/2015 |

* cited by examiner

1) Triangle within slicing plane
2) One vertex in splicing plane
3) One edge in slicing plane
4) One edge in plane, opposite edge intersects with plane
5) Two edges intersect with plane

| Fill line serial | Coordinates of intersection point stored in element of row | | | |
|---|---|---|---|---|
| L1 | 1 | 2 | ... | M |
| L2 | 1 | 2 | ... | M |
| ⋮ | ⋮ | ⋮ | ⋮ | ⋮ |
| Ln | 1 | 2 | ... | M |

FIG. 17

PEELING TYPE LASER TOOTH PREPARING METHOD, APPARATUS AND DEVICE, AND MEDIUM

CROSS-REFERENCE TO RELATED APPLICATION(S)

This patent application is the U.S. National Phase Entry Under 35 U.S.C. § 371 of International Application No. PCT/CN2018/081698, filed on Apr. 3, 2018, which claims the benefit of priority to Chinese Patent Application No. 201810257517.7, filed on Mar. 27, 2018.

TECHNICAL FIELD

The present invention relates to the field of tooth preparation, and in particular to a lift-off type laser tooth preparing method and an apparatus, a device and a medium thereof.

BACKGROUND

In order to obtain a tooth preparation ready for surgery from a target tooth by laser cutting, the laser tooth preparing process involves laser cutting path planning to produce a high-precision laser focus trajectory.

The purpose of laser cutting path planning for a target tooth is to generate a three-dimensional (3D) laser cutting path; according to this path, a cutting head can direct a laser beam to move in the path to achieve laser tooth preparation. According to a working principle of the cutting head, the cutting head employs a layer-by-layer method in laser tooth preparation. Specifically, the cutting head cuts one layer of a two-dimensional (2D) graph by a dual galvanometer system before it moves the lens to cut the next layer. According to the layer-by-layer laser tooth preparation method, the idea of laser cutting path planning is: first acquiring a geometric model of a dental tissue to be removed; then slicing the geometric model into layers to transform the complex 3D model into multiple layers of 2D cross-sectional contour data; and finally, for each of the layers of cross-sectional contour data generating a laser cutting path. Therefore, a 3D laser cutting path for laser tooth preparation is obtained, which is composed of multiple layers of 2D laser cutting path. In the laser tooth preparation process, the cutting head can use the multiple layers of 2D laser cutting path obtained from path planning to cut the target tooth layer by layer, and finally acquire a tooth preparation.

Existing laser tooth preparation employs the layer-by-laser method. As shown in FIG. 1, a layer-by-layer laser tooth preparing process completely removes all dental tissue excluding a tooth preparation from the target tooth. The laser cutting path planning of the layer-by-layer laser tooth preparation is implemented by: slicing the excess dental tissue (other than a tooth preparation) on the target tooth evenly into a number of layers from the top to the bottom according to a determined thickness, to obtain the same number of layers of cross-sectional contour; and for each of the layers of cross-sectional contour generating a laser cutting path.

The layer-by-layer laser tooth preparing method takes full advantages of the working principle of the cutting head, and thus is easy to implement. However, this method removes all dental tissue excluding a tooth preparation from the target tooth by laser cutting; tooth preparing with this method removes a great amount of dental tissue, and thus is low in efficiency especially when used for molar teeth that are large in size.

SUMMARY OF INVENTION

Technical Problem

Layer-by-layer laser tooth preparing method in relevant art is low in efficiency.

Technical Solution to the Problem

Technical Solution

In a first aspect, an embodiment of the present invention provides a lift-off type laser tooth preparing method, including:
acquiring a first STL model of a target tooth and a second STL model of a tooth preparation for the target tooth;
generating an STL model of a lifted-off surface that has an inverted-cone shape where the cone has a generatrix at a predetermined angle with respect to its axis, and has a base that is a three-dimensional contour of an outer edge of a shoulder of the second STL model;
performing a Boolean operation between the STL model of the lifted-off surface and the first STL model, to obtain a third STL model;
performing a Boolean operation between the second STL model and the third STL model, to obtain a fourth STL model that is to be removed;
generating a multi-layer laser cutting path according to the fourth STL model, so as to control a laser tooth preparing device to perform tooth preparing process on the target tooth according to the multi-layer laser cutting path.

In a second aspect, an embodiment of the present invention provides a lift-off type laser tooth preparing apparatus, including:
an acquisition module, configured to acquire a first STL model of a target tooth and a second STL model of a tooth preparation for the target tooth;
a first generation module, configured to generate an STL model of a lifted-off surface that has an inverted-cone shape where the cone has a generatrix at a predetermined angle with respect to its axis, and has a base that is a three-dimensional contour of an outer edge of a shoulder of the second STL model;
a second generation module, configured to perform a Boolean operation between the STL model of the lifted-off surface and the first STL model, to obtain a third STL model;
a third generation module, configured to perform a Boolean operation between the second STL model and the third STL model, to obtain a fourth STL model that is to be removed;
a fourth generation module, configured to generate a multi-layer laser cutting path according to the fourth STL model, so as to control a laser tooth preparing device to perform tooth preparing process on the target tooth according to the multi-layer laser cutting path.

In a third aspect, an embodiment of the present invention provides a lift-off type laser tooth preparing device, including: at least one processor, at least one memory and a computer program instruction stored in the memory, wherein when executed by the processor, the computer program instruction implements the method in the first aspect.

In a fourth aspect, an embodiment of the present invention provides a computer-readable storage medium, storing a computer program instruction, wherein when executed by the processor, the computer program instruction implements the method in the first aspect.

Advantageous Effects of the Invention

Advantageous Effects

Improved efficiency in tooth preparing process for molar teeth that are large in size.

BRIEF DESCRIPTION OF THE DRAWINGS

Description of the Drawings

Figure 1:
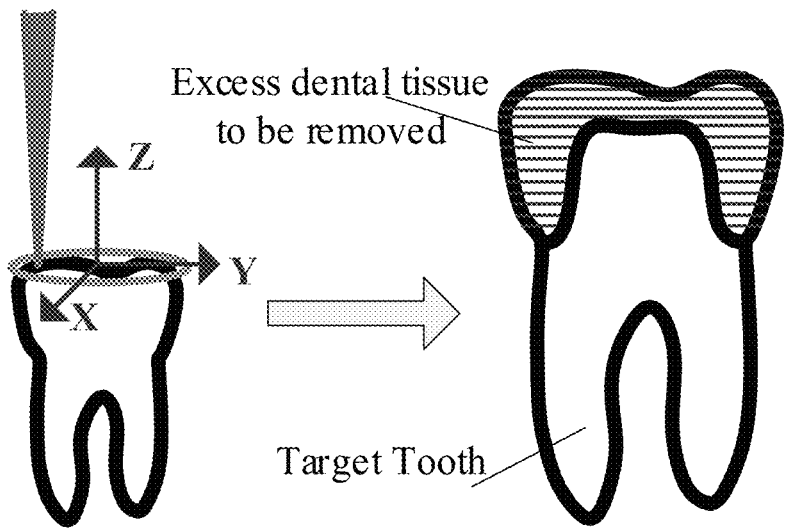

For a better understanding of the present invention, accompanying drawings used in the description of embodiments are briefly described below. It will be apparent to those skilled in the art that the embodiments and drawings described herein are for illustrative purposes only and shall not be construed as limiting. Of the drawings:

FIG. 1 is a schematic diagram of layer-by-layer laser preparing method

Figure 2:
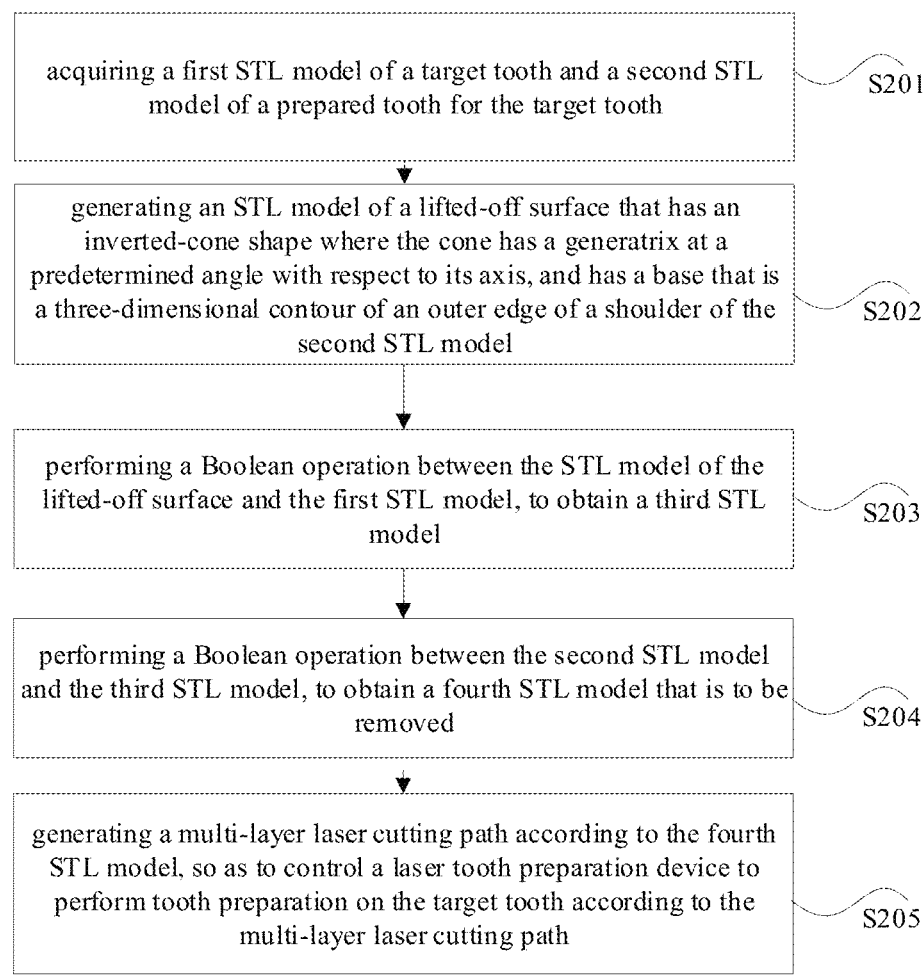
Figure 3:
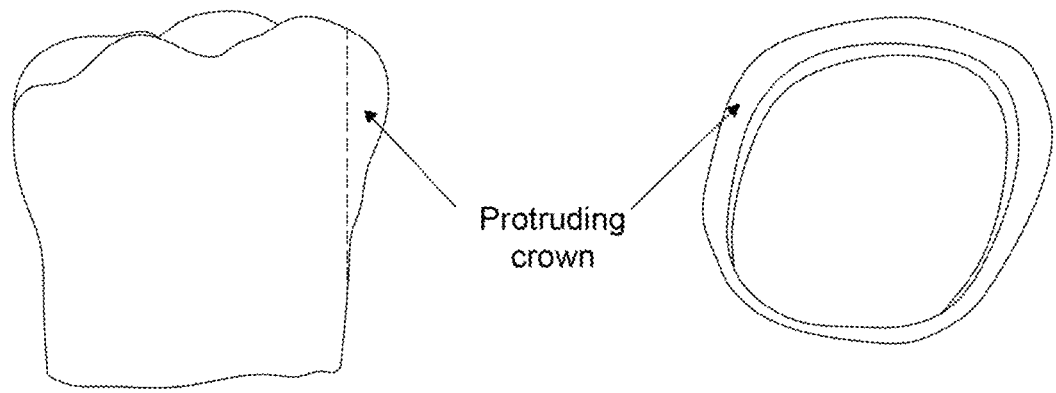
Figure 4:
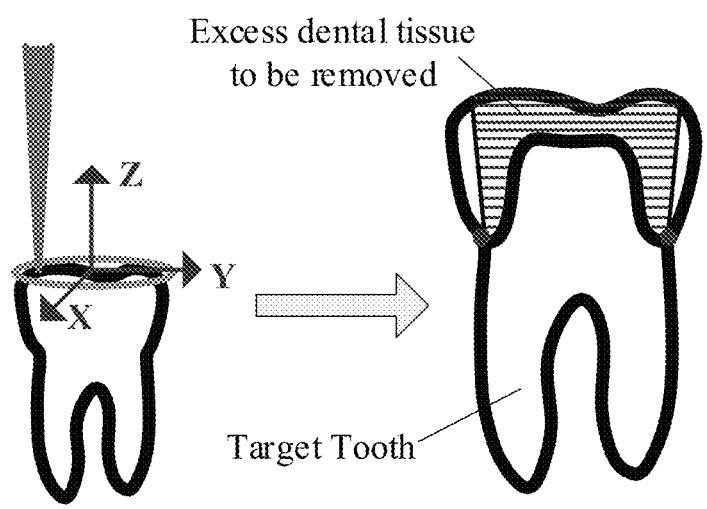
Figure 5:
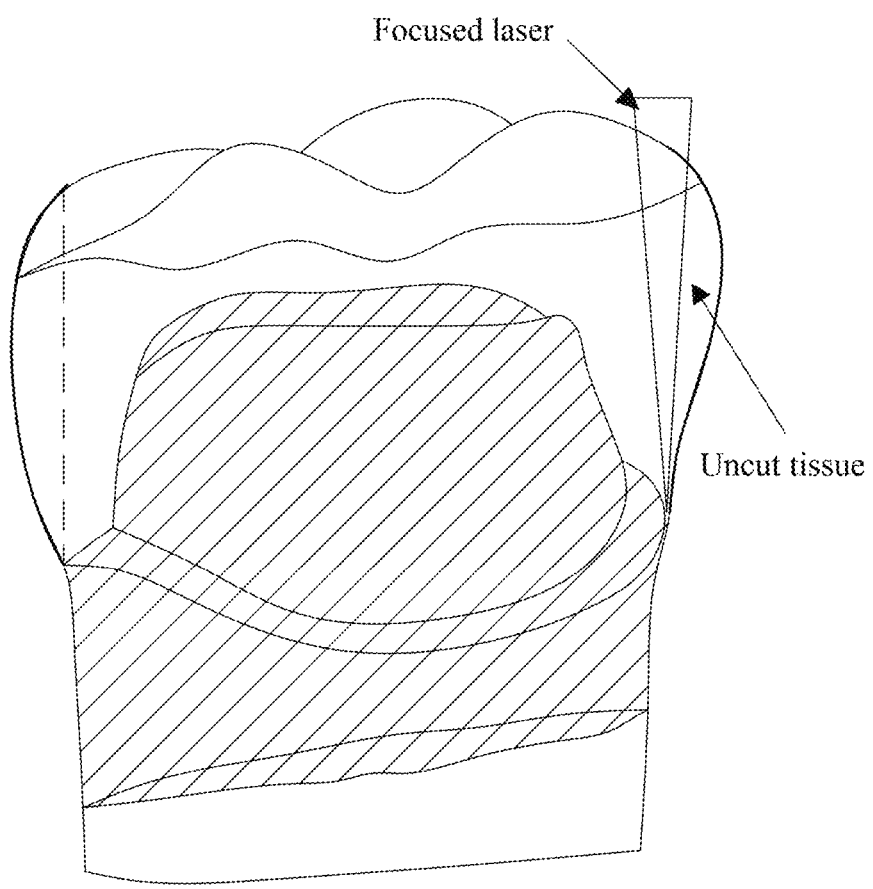
Figure 6:
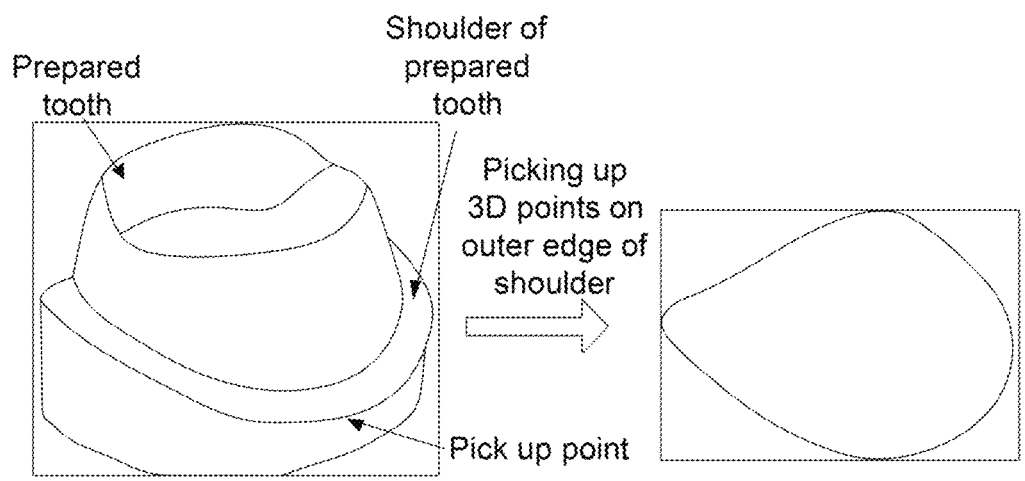
Figure 7:
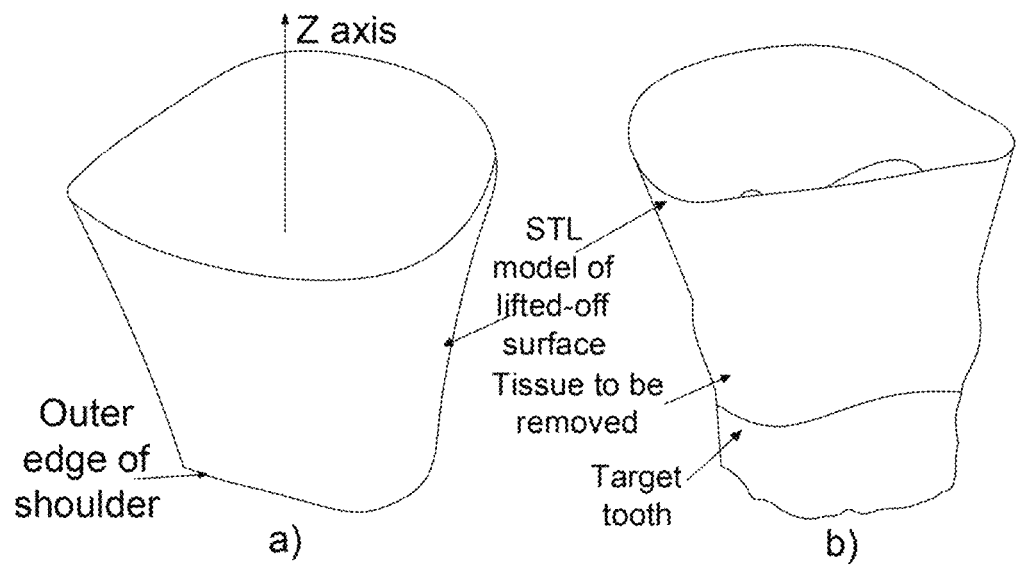
Figure 8:
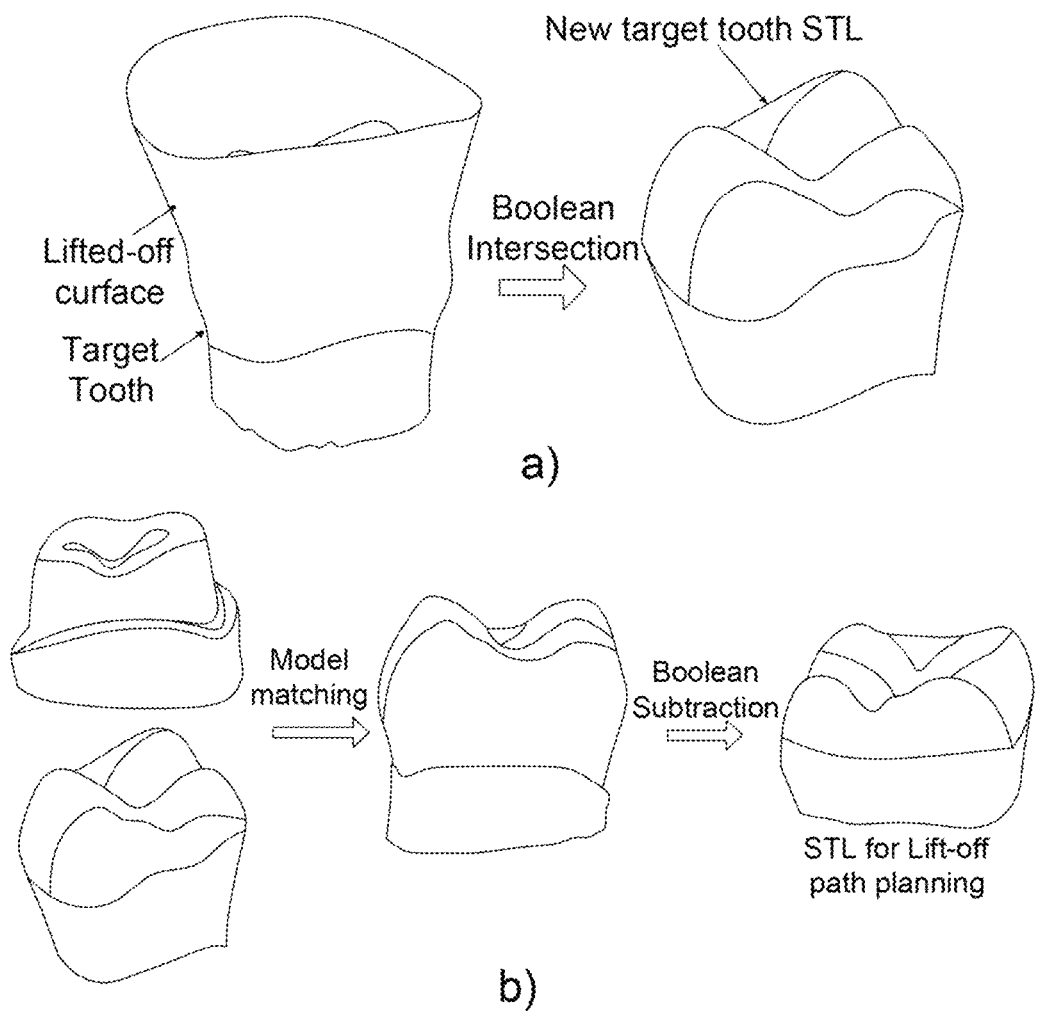
Figure 9:
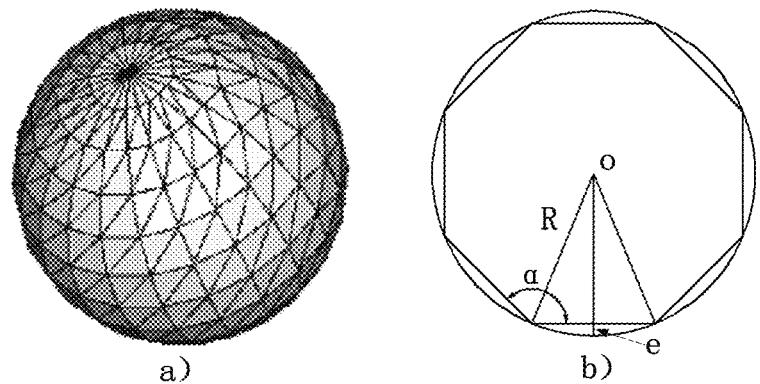
Figure 10:
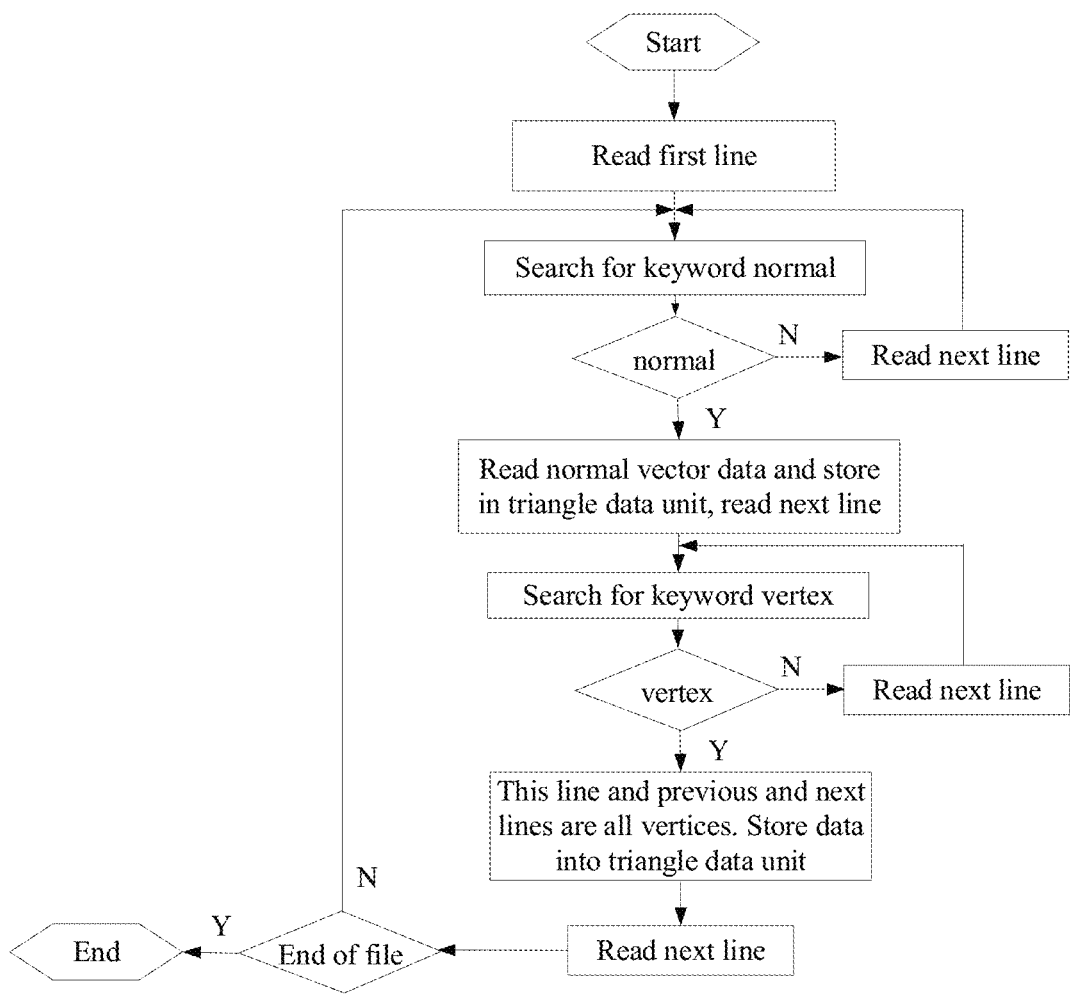
Figure 11:
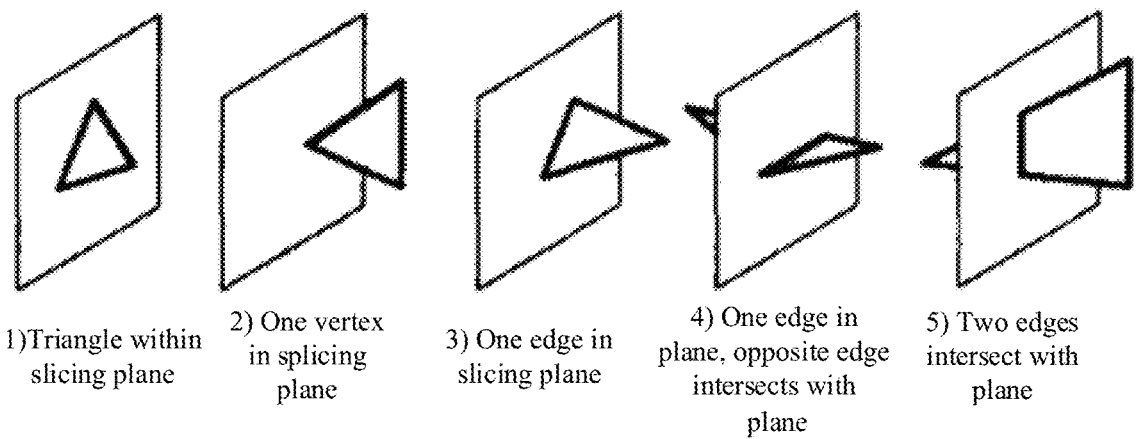
Figure 12:
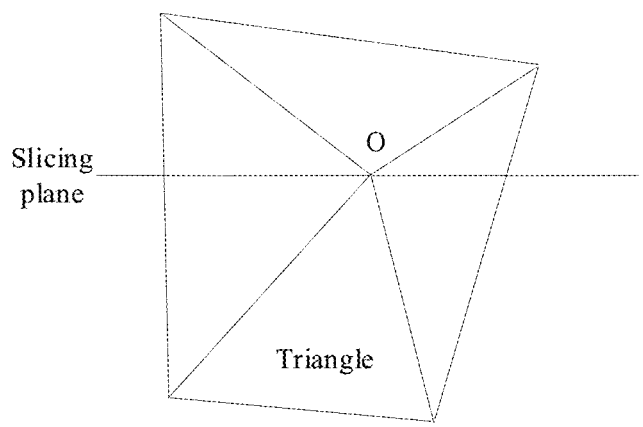
Figure 13:
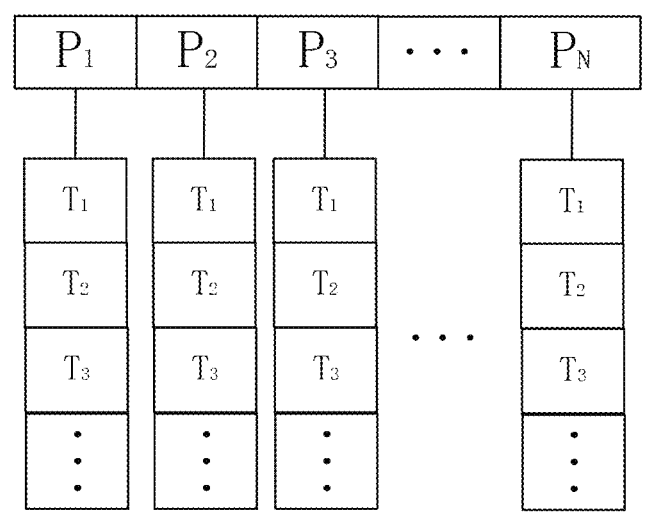
Figure 14:
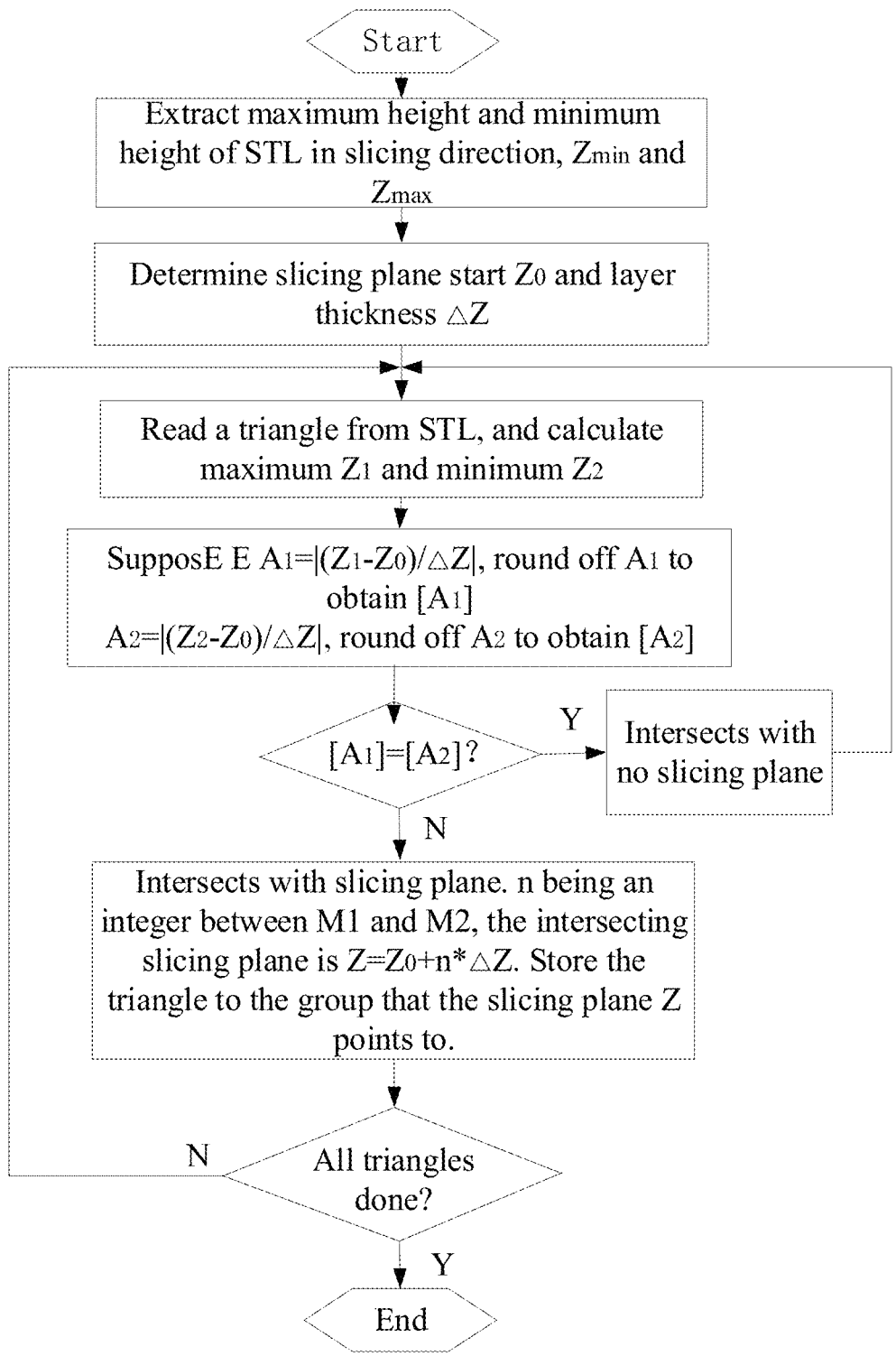
Figure 15:
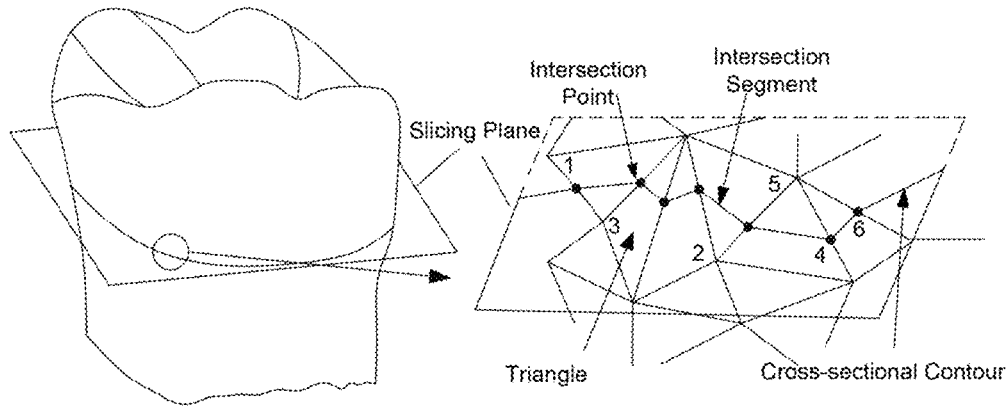
Figure 16:
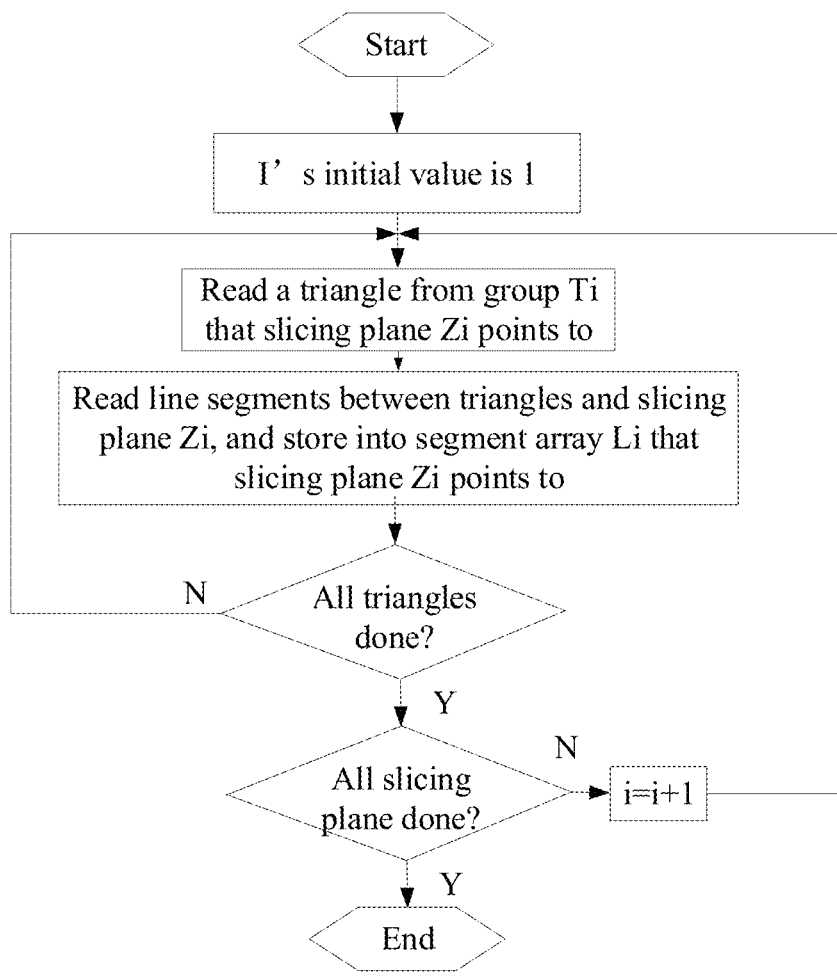
Figure 18:
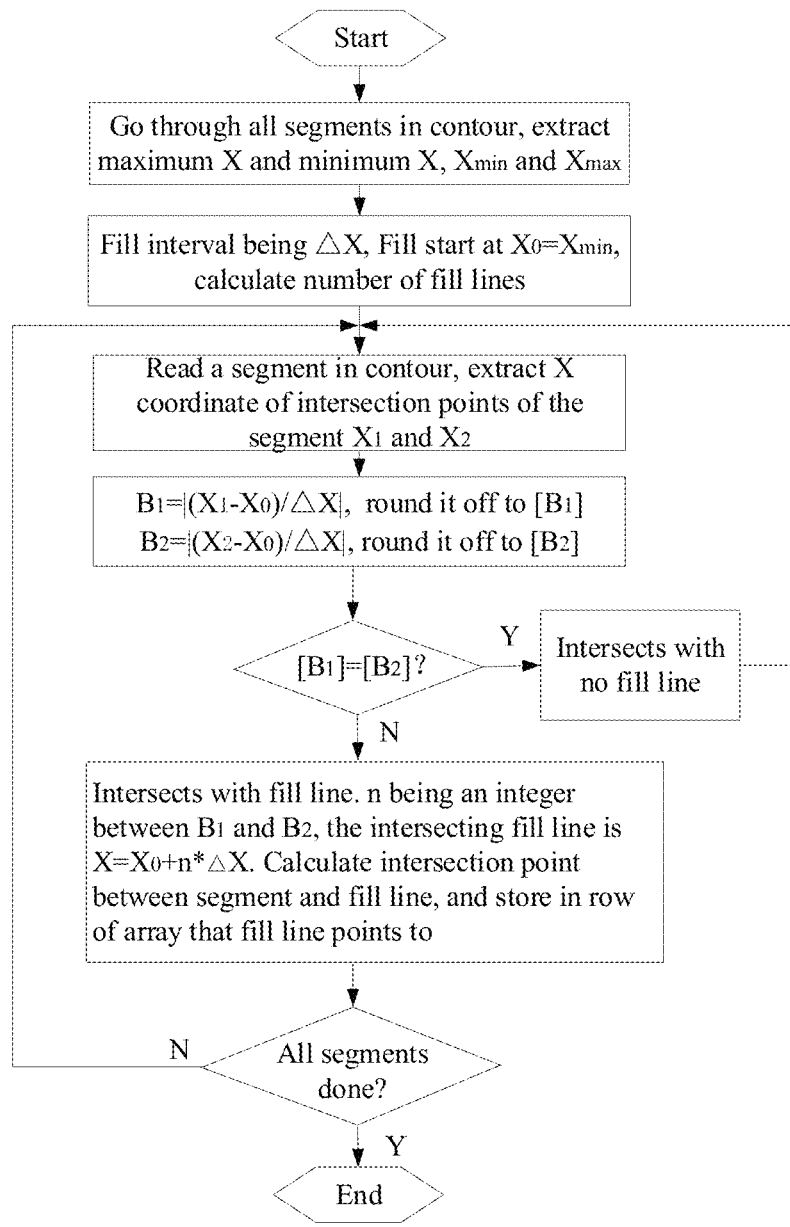
Figure 19:
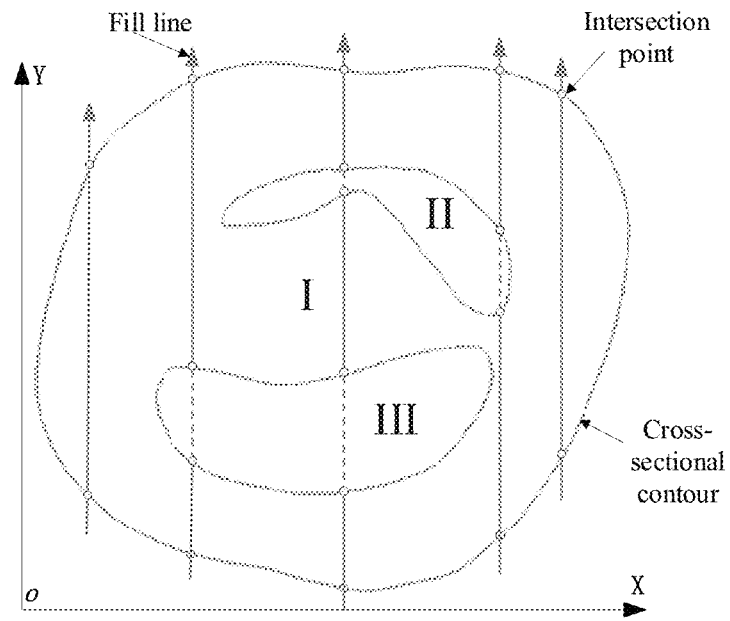
Figure 20:
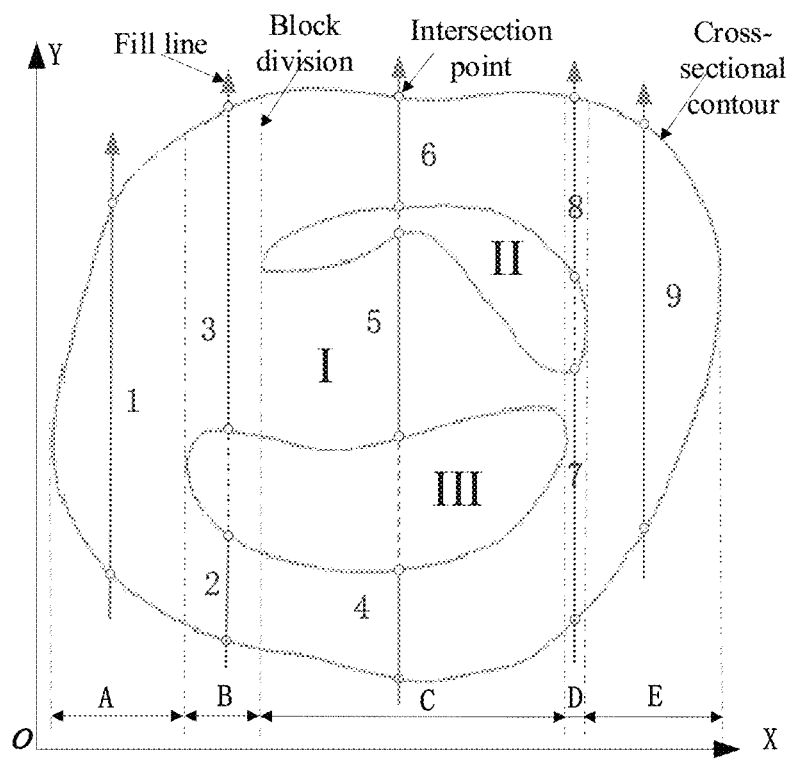
Figure 21:
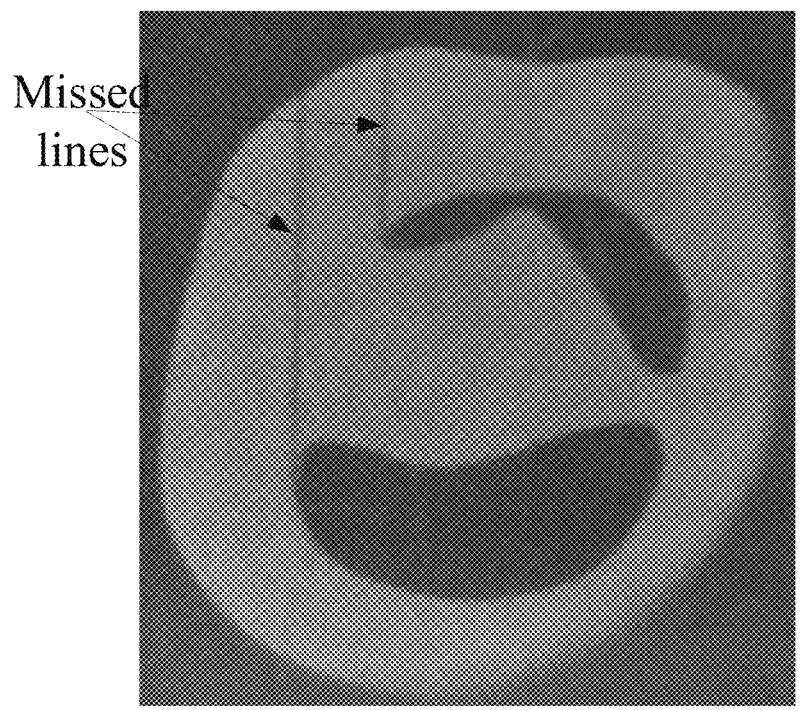
Figure 22:
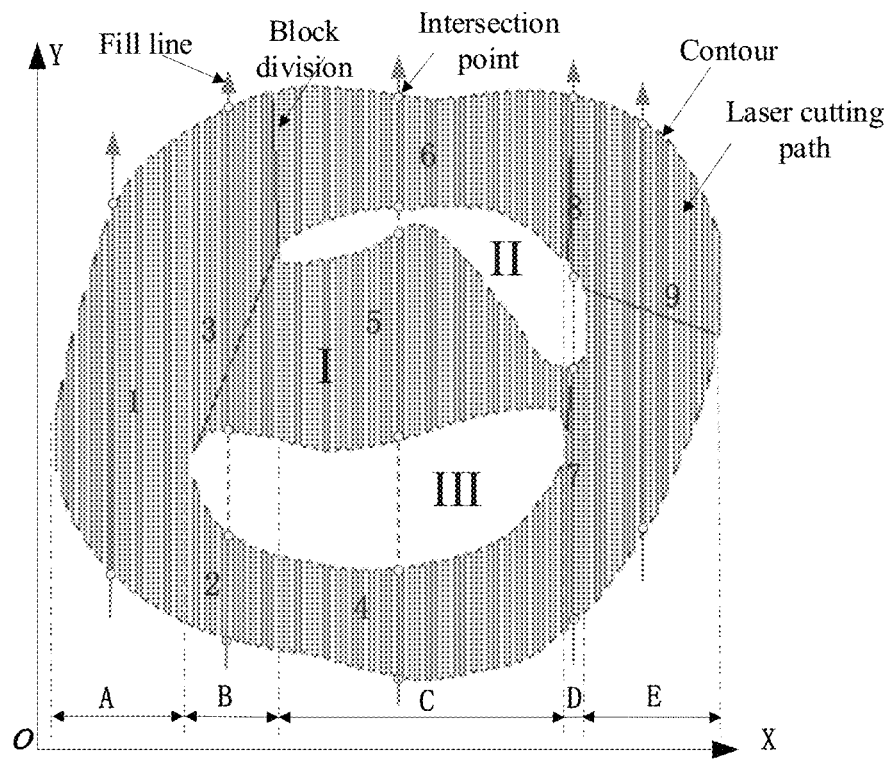
Figure 23:
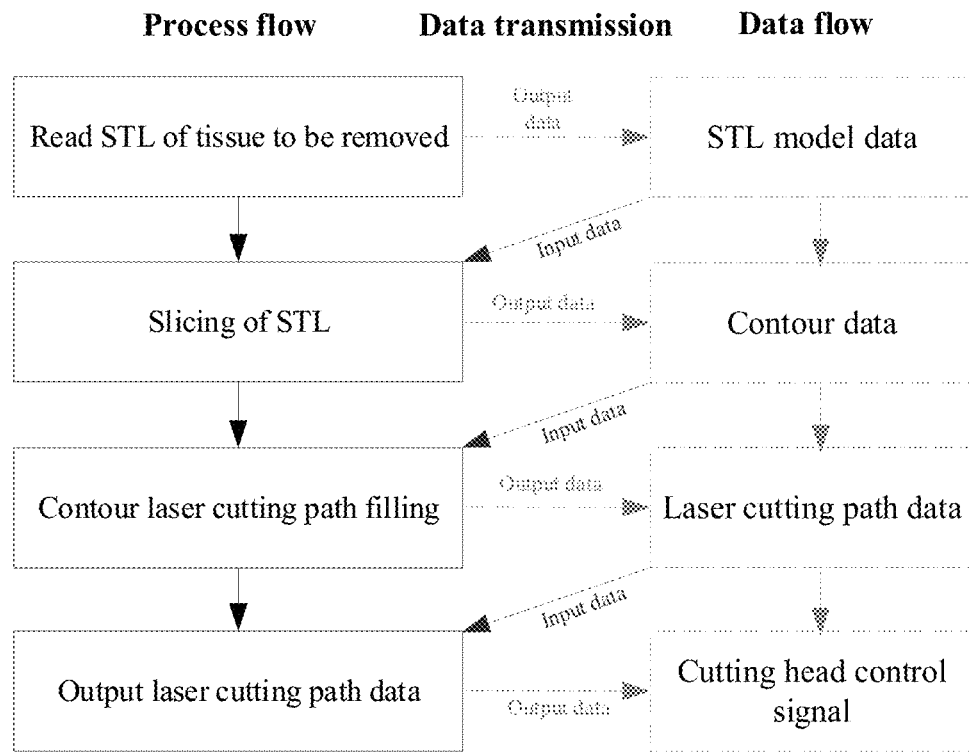
Figure 24:
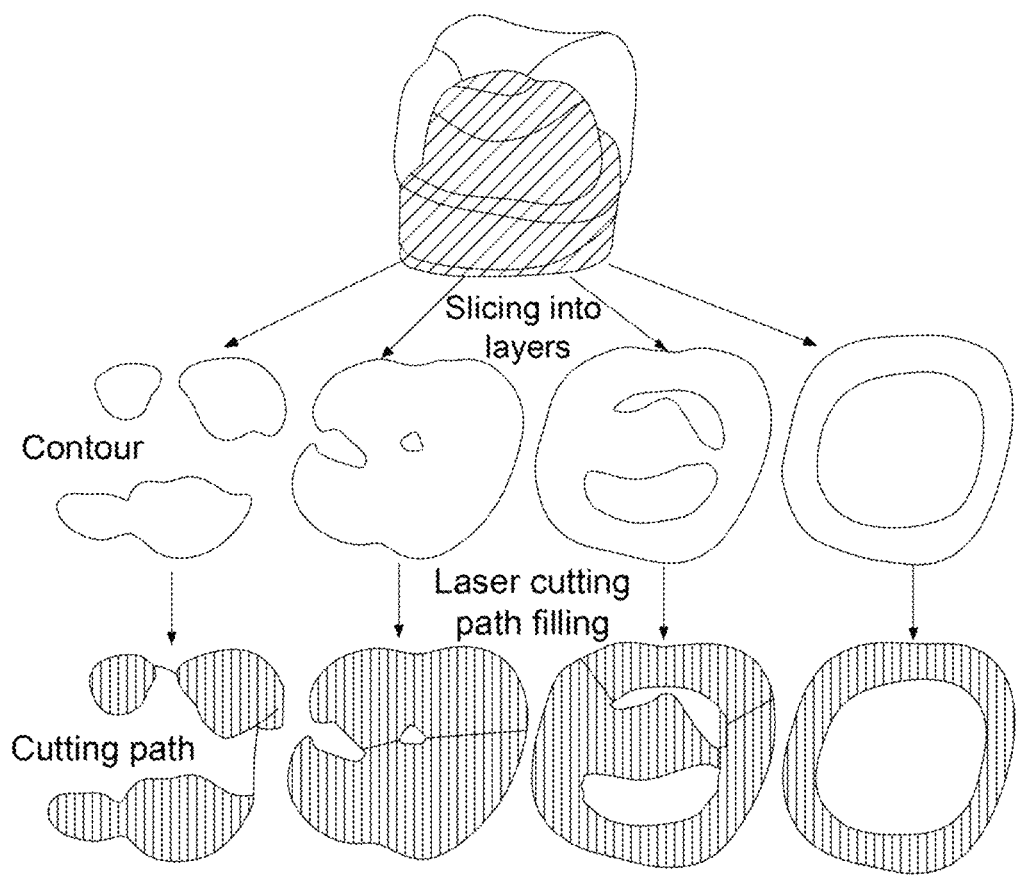
Figure 25:
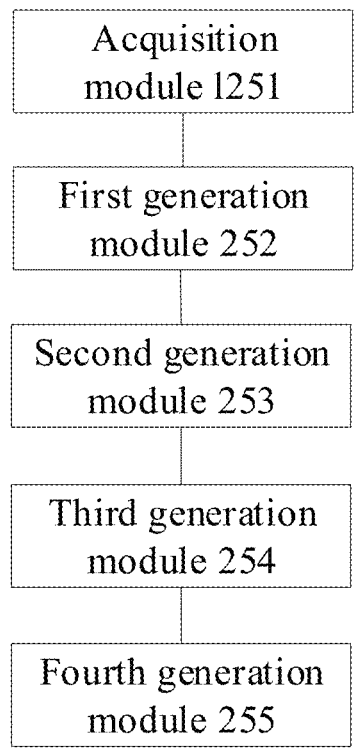
Figure 26:
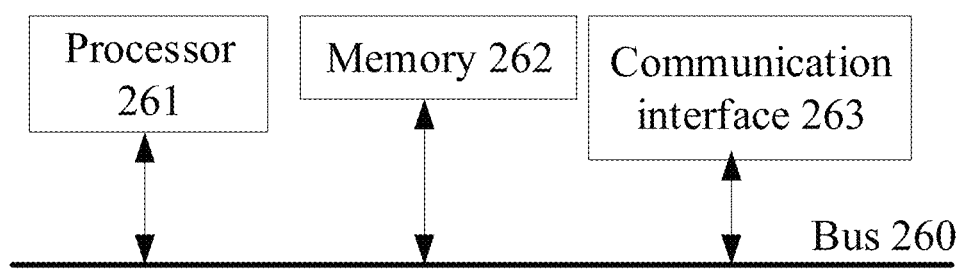

FIG. 2 is a flowchart of a lift-off type laser tooth preparing method according to an embodiment of the present invention;

FIG. 3 is a schematic diagram of a protruding crown of the second molar;

FIG. 4 is a schematic diagram of a lift-off type laser tooth preparing method according to an embodiment of the present invention;

FIG. 5 is a schematic diagram illustrating the occlusion of the laser beam in lift-off type laser tooth preparing process;

FIG. 6 is a schematic diagram illustrating picking up 3D points on the outer edge of the shoulder of a tooth preparation according to an embodiment of the present invention;

FIG. 7 is a schematic diagram illustrating generating an STL model of the lifted-off surface;

FIG. 8 is a schematic diagram illustrating generating an STL model for lift-off type laser tooth preparing method;

FIG. 9 is a schematic diagram illustrating an STL file represents a sphere;

FIG. 10 is a flowchart of reading an STL file;

FIG. 11 is a schematic diagram illustrating five possible positional relationships between a triangle and a slicing plane;

FIG. 12 is a schematic diagram illustrating a slicing plane intersects with triangles sharing the same vertex;

FIG. 13 is a schematic diagram illustrating an array of pointers to structure for storing the grouping data of the triangles according to an embodiment of the present invention;

FIG. 14 is a flowchart of grouping STL model triangles according to an embodiment of the present invention;

FIG. 15 is a schematic diagram illustrating a slicing plane intersects with triangles according to an embodiment of the present invention;

FIG. 16 is a flowchart of generating a non-directional cross-sectional contour according to an embodiment of the present invention;

FIG. 17 is a schematic diagram illustrating a static two-dimensional array of structures according to an embodiment of the present invention;

FIG. 18 is a flowchart of calculating the intersection between fill lines and the cross-sectional contour according to an embodiment of the present invention;

FIG. 19 is a schematic diagram illustrating fill lines in the Y direction intersecting with a cross-sectional contour according to an embodiment of the present invention;

FIG. 20 is a schematic diagram illustrating dividing the laser cutting lines into regions according to an embodiment of the present invention;

FIG. 21 is a schematic diagram illustrating line missing during a laser cutting process;

FIG. 22 is a schematic diagram illustrating generating a laser cutting path based on searching for a best subregion according to an embodiment of the present invention;

FIG. 23 is a schematic diagram illustrating a process flow and a data flow of a laser tooth preparing path planning software according to an embodiment of the present invention;

FIG. 24 is a schematic diagram illustrating cross-sectional contours and laser cutting paths generated by the path planning software according to an embodiment of the present invention;

FIG. 25 is a structural block diagram of a lift-off type laser tooth preparation apparatus according to an embodiment of the present invention;

FIG. 26 is a schematic diagram illustrating a hardware structure of a lift-off type laser tooth preparation device according to an embodiment of the present invention.

DETAILED DESCRIPTION OF PARTICULAR EMBODIMENTS

Preferred Embodiments of the Present Invention

Of the 32 human teeth, some have a protruding tissue on their crowns. FIG. 3 shows a protruding laser dental tissue on the crown of a second molar. In the laser tooth preparation process, the protruding tissue does not need to be cut by laser; instead, an inner tissue is cut, and after tooth preparation steps have completed, the protruding tissue falls off automatically, thereby reducing the amount of dental tissue to be removed by laser. This is the idea of lift-off type laser tooth preparation.

FIG. 4 is a schematic diagram of a lift-off type laser tooth preparation according to an embodiment of the present invention. The laser cutting path planning of the lift-off type laser tooth preparation includes: first lifting, by software processing, a protruding crown off of the three-dimensional model of a target tooth; then slicing the three-dimensional model of the remaining dental tissue into layers; and then generating laser cutting paths for the resulting cross-sectional contours.

It can be seen that the use of the lift-off type method can reduce the amount of dental tissue to be removed by laser in tooth preparation and improve efficiency in tooth preparation.

Studies show that in the process of lift-off type laser tooth preparation, the uncut protruding tissue may occlude the laser beam, as shown in FIG. 5, which prevents the laser from cutting the excess tissue at the bottom. Therefore, for laser tooth preparation with the lift-off type method, the effect of the occlusion of the laser beam needs to be addressed.

1. Lift-Off Type Laser Tooth Preparation STL Model

Compared with layer-by-layer laser tooth preparation, the acquiring of an STL model for lift-off type laser tooth preparation is more complex. First, the STL model of the target tooth is trimmed; and the subsequent steps are similar to those of the STL acquiring method for layer-by-layer laser tooth preparation. The process of trimming a target tooth STL model is described in detail below.

(1) generating a 3D contour for the outer edge of the shoulder of a tooth preparation;

First a 3D contour of the outer edge of the shoulder of a tooth preparation is obtained, which may specifically include: as shown in FIG. 6, picking up 3D points at a determined distance on the outer edge of the shoulder of a tooth preparation in the software Imageware; and connecting the points in sequence, to obtain the 3D contour of the outer edge of the shoulder.

(2) generating an STL model for the lifted-off surface;

The steps for generating an STL model of the lifted-off surface may include: as shown in FIG. 7(a), generating a 3D surface STL model that has a cone-like shape, is at a certain angle with respect to the Z axis, and has a base that is the 3D contour of the outer edge of the shoulder. The purpose of generating the STL model of the lifted-off surface is to perform a Boolean operation between the STL model of the lifted-off surface and an STL model of a target tooth, so that dental tissue that does not need to be cut by laser is lifted off of the target tooth STL. This is shown in FIG. 7(b). In order to address the occlusion of the laser beam, the lifted-off surface is generated such that it is at a certain angle with respect to the Z axis, so that the laser can cut the excess tissue at the bottom.

(3) generating an STL model for lift-off type laser tooth preparation.

First, as shown in FIG. 8(a), a Boolean operation is performed between the STL model of the lifted-off surface generated in the previous step and a target tooth STL, to trim off the protruding tissue on the crown and obtain a new target tooth STL model. Then, as shown in FIG. 8(b), an intersection Boolean operation is performed between the new target tooth STL model and an STL model of the tooth preparation, to finally obtain the STL model that is required for lift-off type laser tooth preparation.

Because tooth preparation requires a high precision, the STL model for laser tooth preparation path planning requires a high precision, leading to a larger number of triangles for the STL model, which is more than 500,000. The complexity of the 3D form of teeth also results in high complexity of the cross-sectional contours of the triangles. These characteristics of the STL model increases the difficulties of layer slicing and laser cutting path generation for single layers in path planning, and reduces the efficiency of the entire path planning process.

2. STL Model Reading

The key to laser tooth preparation path planning is to slice the 3D model of the dental tissue to be removed into layers to obtain 2D contour information of the single-layer section, and then perform laser cutting path generation on the cross-sectional contours according to processing requirements. A 3D model file is a carrier of 3D model data, and 3D model files of different types may employ different modeling methods or different data structures. Therefore, the type of the 3D model file impacts path planning significantly. In the automated laser tooth preparation system, a 3D model file in the STL format is used to store tooth geometric model information.

The STL (Streo Lithographic) format was released by 3D Systems in 1987, and has become the most commonly used format and de facto interface standard in the field of rapid prototyping technologies. It has numerous applications in reverse engineering, finite element analysis, medical imaging, cultural relics protection, etc. FIG. 9(a) shows an STL file representing a sphere. A triangle is a unit; the STL file describes approximately the surface of a 3D object by a large number of connected triangles. Model data includes the three components of a normal vector (determining a positive or negative direction of a triangle) to the triangle, and the coordinates of the three vertices of the triangle. A complete STL file records the normal vector data and vertex coordinate data of all the triangles that make up the object. Currently the STL format can be binary or ASCII (as illustrated in the embodiments of the present disclosure).

As shown in FIG. 9b, the accuracy of an STL model is determined by an arc height e and the cosine of an angle $\alpha$. Arc height is the distance between an arc's chord and the highest point on the arc; as the chord is used as an approximation of the arc, the smaller the arc height, the more accurate the approximation. The cosine of the angle $\alpha$ is the cosine of the angle between two adjacent straight lines that approximate to the arc; the closer the cosine of the angle is to 1, the more accurate the approximation is. In general, the more triangles used in an STL file, the higher the degree of approximation of the model and the higher the accuracy of the model. When the density of the triangles reaches its limit, the representation includes each and every point on the surface. However, if the accuracy is too high, the number of triangles in the file is too large and data processing time and memory consumption of the computer are increased. In practical applications, it is preferable to use as few triangles as possible to represent the object surface, so long as the accuracy requirement is met.

ASCII STL files provide tessellated model data line by line, and each line is indicated by a key word. Binary STL files describes geometric information of the triangles with a fixed number of bytes. Binary STL files are small (usually ⅕ of the ASCII ones), but the ASCII format is intuitive and easy to read, write and modify. Therefore, in this specification the ASCII STL file is used. An ASCII STL file has the following structure:

| | |
|---|---|
| solid filename stl | // beginning of the file, file name |
| facet normal x y z | // three components of the normal vector to a triangle |
| outer loop | |
| vertex x y z | // 3D coordinates of first vertex |
| vertex x y z | // 3D coordinates of second vertex |
| vertex x y z | // 3D coordinates of third vertex |
| end loop | |
| end facet | // end of the definition of first triangle |
| ...... | |
| ...... | |
| ...... | // end of the definition of last triangle |
| end solid filename stl | // end of the file |

The ASCII STL file contains the following keywords: solid identifies the beginning of the file and appears only once in the file; facet normal identifies the normal vector to a triangle, and each triangle has only one normal vector; outer loop identifies the beginning of description of the vertices of the triangle, and the description is in a counter-clockwise order; vertex identifies a vertex and appears three times for one triangle; end loop identifies the end of description of one vertex; end facet identifies the end of description of one triangle; end solid identifies the end of the entire STL file description and only appears once. Model data is read according to the keywords contained in the STL file, and a flowchart of the reading algorithm is shown in FIG. 8.

3. STL Model-Based Slicing

The purpose of slicing is mainly to slice the complex 3D form of the STL model used for path planning into simpler 2D contours, in preparation for the next step of laser cutting path generation for single layers. The slicing process generally includes: first determining a slicing direction; then determining a slicing starting point and a layer thickness value; and then intersecting in the slicing direction the STL model with a series of slicing planes placed at an interval, thereby forming a cross-sectional contour on each slicing plane.

In the automated process of laser tooth preparation, because of the large number of triangles in the STL model, in order to improve the efficiency of the entire tooth preparation process, it is desirable to provide a fast slicing algorithm which can complete the slicing process in a short period of time.

Studies on existing slicing algorithms show that there are three main factors affecting the processing speed of slicing:
(1) judging the positional relationship between a triangle and the slicing plane;
(2) calculating the intersection between the triangle and the slicing plane;
(3) generating a cross-sectional contour. Therefore, to improve the speed and efficiency of STL model slicing, these three main factors must be considered. In order to obtain a high slicing efficiency, an embodiment of the present invention provides a new fast slicing algorithm based on the studies of existing algorithms, which can directly generate non-directional contours, without sorting the intersection segments or rebuilding the topological structure, and without affecting the subsequent laser cutting generation. A basic idea of the algorithm is as follows: First, according to the different slicing planes that the triangles intersect with, dividing all triangles of the STL model into a number of groups where the number of the groups is the same as the number of the slicing planes; then for each group acquiring the intersection segments between the triangles in the group and the corresponding slicing plane, thereby obtaining a non-directional, closed, cross-sectional contour without sorting by taking advantage of the continuity between the triangles.

(1) Grouping the STL Model Triangles

In the fast slicing algorithm according to an embodiment of the present invention, the triangles of the STL model are grouped based on the slicing plane that a triangle intersects with; as a result, the slicing process includes a step for judging the intersections between the triangles and the slicing planes. Firstly, the positional relationships between triangles and slicing planes are analyzed. There are five possible positional relationships between a triangle and a slicing plane, as shown in FIG. 11. In the algorithm according to an embodiment of the present invention, when judging the positional relationships between the triangles and the slicing planes, only the situations where an edge intersects with the slicing plane are considered, in other words, situations 1) and 2) in FIG. 11 can be ignored without affecting the structure of the grouping. Generally speaking, situation 1) does not occur between slicing planes and triangles. And the reason for ignoring situation 2) is, in an STL model a vertex is shared by at least three triangles, and if one of the triangles intersects with a slicing plane in situation 2), then one of the other triangles sharing the same vertex has an intersection relationship with the slicing plane in one of situations 3), 4) and 5). This is shown in FIG. 12.

Before grouping, a data structure may be designed to store the grouping data of the triangles. As shown in FIG. 13, the designed data structure is an array of pointers to structure. The dimension of the array equals the number of the slicing planes. Each element in the array corresponds to one slicing plane, and points to a set of triangles that intersect with the slicing plane.

In the new slicing algorithm, the grouping the STL model triangles may specifically include the following steps:

(i) determining a slicing direction, and extracting a maximum height and a minimum height of the STL model in the slicing direction;

(ii) determining a layer thickness and a slicing starting point, and accordingly acquiring the number of slicing planes N;

(iii) reading one triangle of the STL model, first calculating a maximum value and a minimum value of the triangle in the Z direction; then according to the slicing starting point and the slicing interval, judging whether the triangle intersects with a slicing plane, and if it intersects, acquiring the slicing plane, and storing the triangle into a linked list that the slicing plane points to;

(iv) for every triangle of the STL model, performing the process in (3), to divide the triangles into a number of groups where the number of the groups is the same as the number of the slicing planes.

FIG. 14 shows a detailed flowchart of the process for grouping triangles.

As can be seen from the grouping process of the new algorithm, by only two iterations with the triangles, all triangles of the STL model are divided into a number of groups where the number of the groups is the same as the number of the slicing planes, which greatly improves the efficiency of grouping. Moreover, by this grouping method, all triangles that intersect with the same slicing plane are placed in the same group. Therefore, when calculating the cross-sectional contours, the positional relationships between the slicing planes and the triangles no longer need to be judged; and the intersections between the slicing planes and the triangles can be calculated directly.

(2) Generating a Non-Directional Cross-Sectional Contour

A non-directional cross-sectional contour means that the arrangement of the intersection segments that make up the cross-sectional contour is without ordering. As compared with a directional cross-sectional contour, the non-directional cross-sectional contour is easier to generate because it does not require the sorting of the intersection segments. FIG. 15 shows a schematic diagram where a slicing plane intersects with six triangles of a target tooth STL model. According to the grouping situation, these six triangles belong to a group that the slicing plane points to. The intersection between each triangle and the slicing plane results in an intersection segment; and the six intersection segments form a non-directional cross-sectional contour.

When the STL model is closed, an intersection operation is performed between every triangle of the STL model that intersects with the slicing plane and the slicing plane, and the resulting intersection segments form a non-directional, closed cross-sectional contour.

According to the triangle grouping results, each slicing plane points to a unique set of triangles, and the triangles in the group are the set of all triangles that intersect with the slicing plane in the STL model. Moreover, because the STL model for laser tooth preparation path planning is closed, all triangles that intersect with the splicing plane are continuous. Therefore, when an intersection operation is performed between a slicing plane and every triangle of the group that the slicing plane points to, the resulting intersection segments form a closed, non-directional cross-sectional contour. FIG. 16 is a detailed flowchart of the process for generating a non-directional cross-sectional contour.

It can be seen that the generation of a non-directional cross-sectional contour is much simpler than the generation of a directional cross-sectional contour, which takes advantage of the continuity between the triangles, avoids judging the positional relationship between the slicing plane and the triangle, avoids sorting the generated intersection segment, simplifies the slicing process, improves the efficiency of the slicing process, and simplifies the slicing procedure.

4. Single-Layer Laser Cutting Path Filling Algorithm

The purpose of single-layer laser cutting path filling is to perform a laser cutting line filling process on the cross-sectional contour obtained from slicing, and to finally generate path planning data that can be used by the cutting head. Because the cross-sectional contour generated from slicing is non-directional, and the number of intersection segments in the cross-sectional contour is huge, it is desirable to process the non-directional cross-sectional contour at a high efficiency in the single-layer laser cutting path filling, to finally generate a high-quality laser cutting path.

Based on parallel line filling algorithm and its derivative algorithms, an embodiment of the present invention provides a new laser cutting path filling algorithm, which can fill the non-directional cross-sectional contour and generate a high-quality high-efficiency single-layer laser cutting. A main idea of the algorithm is as follows: first calculating intersection points between fill lines and the non-directional cross-sectional contour; then dividing according to the obtained intersection points; and then searching, by starting at an initial cutting region and in a progressive fashion, for a best cutting region according to a determined criterion, thereby finally generating a high-efficiency laser cutting path. The laser cutting path filling algorithm according to an embodiment of the present invention is described in detail as follows.

(1) Calculating the Intersection Between Fill Lines and the Non-Directional Cross-Sectional Contour In the parallel line filling algorithm, fill lines can be in X direction or Y direction, i.e., the fill lines are parallel to the positive direction of X-axis or the positive direction of Y-axis. In this embodiment of the present invention, the direction of the fill lines is Y direction. Because the cross-sectional contour is filled with intersection segments, calculating the intersections between the fill lines and the cross-sectional contour can then be converted into calculating the intersection between the fill lines and the intersection lines.

Before the intersection calculation, a data structure is designed to store the intersection points between the fill lines and the intersection segments. As shown in FIG. 17, a static two-dimensional array of structures is used to store the intersection point data. Each element of the array is an intersection point structure, storing the coordinates of the intersection point. The number of rows in the two-dimensional array is the number of fill lines intersecting with the cross-sectional contour. The number of columns in the array is the maximum number of intersection points between a fill line and the cross-sectional contour. All intersection points between a fill line and the cross-sectional contour are stored in a row of the array that corresponds to the fill line and is with the same sequence number.

The calculating the intersection between fill lines and the cross-sectional contour includes:
 i. going through the cross-sectional contour to acquire a maximum X coordinate and a minimum X coordinate of the cross-sectional contour;
 ii. setting the coordinates of a start of the fill lines, and calculating the number of fill lines that intersect with the cross-sectional contour according to a fill line distance;
 iii. for one intersection segment in the cross-sectional contour, calculating whether the intersection segment intersects with a fill line and intersects with which fill line according to the x-coordinates of the two end points of the segment, and if the intersection segment intersects with a fill line, calculating the intersection point and storing the intersection point in a row of the array with the same sequence number as the fill line;
 iv. for every intersection segment in the cross-sectional contour, performing the process in iii, to complete the calculating of the intersection between fill lines and the cross-sectional contour.

FIG. 18 shows a detailed flowchart of the process for calculating the intersection between fill lines and the cross-sectional contour.

Similar to the grouping principle of slicing, by only two iterations with the intersection segments in the cross-sectional contour, the intersection between all fill lines and the cross-sectional contour can be calculated, which is more efficient than other algorithms.

(2) Extracting Laser Cutting Lines

Upon completion of calculating the intersection between fill lines and the cross-sectional contour, the obtained intersection point data are processed to extract laser cutting lines.

In the result from the calculating the intersection between fill lines and the cross-sectional contour, in the two-dimensional array of structures for storing the intersection point data, the elements stored in each row are all the intersection points between the fill line with the same sequence number as the row and the cross-sectional contour. The intersection points stored in each row is not sorted; the intersection points in each row is to be sorted in ascending order of the Y coordinate.

FIG. 19 is a schematic diagram illustrating fill lines in the Y direction intersecting with a cross-sectional contour. In the figure, the cross-sectional contour has three regions I, II and III. The region I is to be cut by laser, and the closed regions II and III are not to be cut. As can be seen from FIG. 46, for a closed cross-sectional contour graph, the number of the intersection points between a fill line and the cross-sectional contour is an even number; and the segment between the first and the second intersection points of the fill line and the cross-sectional contour is a laser cutting line, the segment between the second and third intersection points is not a laser cutting line, the segment between the third and fourth intersection points is a laser cutting line. Hence, the segment between the 2ith and (2i+1)th intersection points is a laser cutting line; while the segment between the (2i+1)th and (2i+2)th intersection points is not a laser cutting line. By using the rules above, laser cutting lines can be extracted from the sorted row.

(3) Dividing the Laser Cutting Lines Into Regions

This section mainly discusses how to divide the extracted laser cutting lines into regions, so that the complex laser cutting region is divided into simple subregions.

FIG. 20 shows an example of the idea of dividing the laser cutting lines into regions. Specifically, the laser cutting region I in the figure is a collection of laser cutting lines, therefore dividing all laser cutting lines is to divide the laser cutting region I. First, according to the change in the number of intersection points between the fill line and the cross-sectional contour, the laser cutting region I shown in FIG. 20 is divided into five blocks A, B, C, D and E: in block A, the fill line and the cross-sectional contour have two intersection points; in block B, the fill line and the cross-sectional contour have four intersection points; in block C, the fill line and the cross-sectional contour have six intersection points; in block D, the fill line and the cross-sectional contour have four intersection points; in block E, the fill line and the cross-sectional contour have two intersection points. Then the blocks are further divided: if the number of intersection points between the fill line and the cross-sectional contour in a block is greater than 2, then the laser cutting lines in the block can be divided into smaller areas. Specifically, the laser cutting lines between the 2ith and the (2i+1)th intersection points can be regarded as an independent area. By using the dividing method above, block C in FIG. 20 can be divided into three independent subregions 4, 5, and 6. By using the dividing method above, the laser cutting region I in the cross-sectional contour shown in FIG. 20 can be divided into 9 subregions 1-9, thereby completing the dividing the laser cutting lines of one cross-sectional contour layer into regions.

According to the laser cutting line division idea above, a general process for dividing laser cutting lines of a cross-sectional contour into regions include:
(i)
First, dividing a row of the array into blocks according to the change in the number of intersection points stored in the row of the two-dimensional array of structures;
(ii)
Then further dividing the intersection point data in each block of the row of the array. For each block, extract the first and second intersection points as one subregion, extract the third and fourth intersection points as another subregion, and repeat until all intersection points are processed. The intersection point data of each subregion is stored into a one-dimensional array of structures.

(4) Generating a Laser Cutting Path

In the result from laser cutting line division, each subregion obtained is monotonic. Therefore, by sorting the generated monotonic subregions in a certain order, a complete laser cutting path can be generated.

Laser jump refers to the action that the laser takes when it encounters a part that does not need to be cut; the laser jumps off at a speed that is several times the speed of cutting. A high-quality laser cutting path requires minimum number and distance of laser jumps, because high-speed high-frequency laser jumps cause the motor to start and stop and frequently change its speed, which will ultimately reduce the life cycle of the equipment. Therefore, when generating a laser cutting path based on subregions, the number and distance of laser jumps should be kept as low as possible, so as to obtain a high-quality laser cutting path. Moreover, the distance of jumps in the direction perpendicular to the fill lines should also be kept as low as possible, because when the distance in the direction perpendicular to the fill lines is high, line missing may occur in laser cutting; an example of missed lines is shown in FIG. 21.

Therefore, in generating a laser cutting path, the distance of jumps in the direction perpendicular to the fill lines should be minimized, and the number and distance of laser jumps should be minimized. In order to reduce the number and distance of laser jumps, an embodiment of the present invention provides a method for generating a high-quality laser cutting path based on searching for a best subregion, where the best subregion meets the following criteria: a. The distance of laser jumps in the direction perpendicular to the fill lines is minimum; b. The distance of laser jumps is minimum; and Criterion a is given a higher priority than criterion b. Specifically, the process of generating a laser cutting path may include:
  i. regarding the first subregion in the result from laser cutting line division as a first cutting region;
  ii. by starting at a last point in the first cutting region, searching for a best subregion from the rest subregions according to the criteria above, and taking the search result as a second cutting region;
  iii. by starting at a last point in the second cutting region, searching in the rest subregions; repeating until there is no subregions left, thereby obtaining a laser cutting path for the whole cross-sectional contour.

According to the method above for generating a laser cutting path, a laser cutting path is generated for the cross-sectional contour in FIG. 19, and the obtained path is shown in FIG. 22. The cutting path is in the order: 1→2→4→7→9→8→6→3→5. This cutting order has fewer laser jumps and a shorter distance, which improves the efficiency of laser cutting. This can prove the advantage of the algorithm.

5. Laser Tooth Preparation 3D Path Planning Software and Algorithm Verification

In order to verify the path planning algorithm and the experimental study of laser tooth preparation provided by the embodiment of the present invention, a laser tooth preparation 3D path planning software is written in a Visual 6.0 programming environment, and the software is used to test the slicing of an STL model of a dental tissue to be removed and to test laser cutting path filling of a cross-sectional contour obtained from the slicing.

Laser Tooth Preparation 3D Path Planning Software

According to the laser tooth preparation 3D path planning algorithm above, a laser tooth preparation 3D path planning software is written. Main functions of the software include:

i. reading a tooth STL model file with a large amount of data; ii. slicing the the STL model into layers; iii. performing laser cutting path filling on the cross-sectional contour generated from slicing; iv. generating a laser cutting path data file that can be used directly by a laser cutting head control system. In addition, the software may also be capable of displaying STL models, cross-sectional contours and laser cutting paths, and performing rotate, move and zoom operations on the graphs above.

FIG. 23 shows a process flow and a data flow of the laser tooth preparation path planning software. First, read an STL file of a dental tissue to be removed, thereby obtaining data of the STL model, which is made up of triangles. Then slice the obtained STL model data to convert 3D model data contained in the STL model into 2D cross-sectional contour data; the cross-sectional contour is made up of line segments. Then cross-sectional contour laser cutting path filling operation, which is to identify laser cutting regions from the 2D cross-sectional contour data generated from the slicing, fill a laser cutting path and generate laser cutting path trajectory data; the laser cutting path is made up of points. Finally, output the laser cutting path data in a text format to the control system of the laser cutting head, which converts it into a control signal to control the movement of the laser cutting head.

Path Planning Algorithm Verification

In order to verify the path planning algorithm provided by the embodiment of the present invention, the laser tooth preparation software is used to test the STL model slicing and the cross-sectional contour laser cutting path filling. FIG. 24 shows cross-sectional contours and corresponding laser cutting paths generated from the test. The total number of triangles in the STL model is 755044, and the three-dimensional form is complex. From the test results, it can be concluded that the slicing algorithm provided by the embodiment of the present invention can effectively slice an STL model having a large number of triangles to obtain a correct cross-sectional contour. In addition, it takes 8.06 s to generate a 100-layer cross-sectional contour; the algorithm is efficient. The laser cutting path filling algorithm provided by the embodiment of the present invention can generate a high-quality laser cutting path from a non-directional cross-sectional contour, and the number of laser jumps is small, and without line missing. This algorithm is suitable for cross-sectional contours with different complexities. Therefore, the laser cutting path filling algorithm provided by the embodiment of the present invention is correct and efficient.

EXEMPLARY EMBODIMENTS OF THE INVENTION

Embodiments of the Present Invention

Features and exemplary embodiments of various aspects of the present invention will be described in detail below. In order to make the objectives, technical solutions and advantages of the present invention clearer, the present invention will be further described in detail below with reference to the accompanying drawings and embodiments. It should be understood that the specific embodiments described herein are only used to explain the present invention, and are not intended to limit the present invention. It will be apparent to those skilled in the art that the present invention may be practiced without the need for some of these specific details. The following description of the embodiments is provided merely to provide a better understanding of the present invention by showing examples of the present invention.

It should be noted that in this specification, relational terms such as first and second are used only to distinguish one entity or operation from another entity or operation, and do not necessarily require or imply that there is any such actual relationship or order between these entities or operations. Moreover, the terms "including", "comprising" or any other variation thereof are non-exclusive, such that a process, method, article or device that includes a series of elements includes not only those elements but also other elements that are not explicitly listed, or elements that are inherent to such processes, methods, articles or device. Unless otherwise limited, defining an element with the phrase "comprising . . . " does not exclude the case where the process, method, article or device comprises more of the same element.

An embodiment of the present invention provides a lift-off type laser tooth preparation method. FIG. 2 is a flowchart of the lift-off type laser tooth preparation method according to the embodiment. As shown in FIG. 2, the method includes the following steps:

Step S201: acquiring a first STL model of a target tooth and a second STL model of a tooth preparation for the target tooth;

Step S202: generating an STL model of a lifted-off surface that has an inverted-cone shape where the cone has a generatrix at a predetermined angle with respect to its axis, and has a base that is a three-dimensional contour of an outer edge of a shoulder of the second STL model;

Step S203: performing a Boolean operation between the STL model of the lifted-off surface and the first STL model, to obtain a third STL model;

Step S204: performing a Boolean operation between the second STL model and the third STL model, to obtain a fourth STL model that is to be removed;

Step S205: generating a multi-layer laser cutting path according to the fourth STL model, so as to control a laser tooth preparation device to perform tooth preparation on the target tooth according to the multi-layer laser cutting path.

Optionally, prior to acquiring a first STL model of a target tooth and a second STL model of a tooth preparation for the target tooth, the method may include: acquiring three-dimensional surface data of the target tooth by using a three-dimensional intra-oral scanner, and storing the data as the first STL model; designing based on the first STL model according to clinical requirements to obtain the second STL model.

Optionally, the predetermined angle in the step S202 above is 3° to 10°.

Optionally, the generating a multi-layer laser cutting path according to the fourth STL model in step S205 may be by the same method as a laser cutting path generation method used in a layer-by-layer laser preparation method, for example: slicing the fourth STL model into layers and generating a cross-sectional contour for each layer; for each layer filling the cross-sectional contour with parallel fill lines at a predetermined interval, and extracting a laser cutting path for each layer.

Through the description of the foregoing implementation manners, those skilled in the art can clearly understand that the method according to the foregoing embodiments can be implemented by means of software plus some necessary universal hardware platform, and of course, also by hardware, but in many cases the former is a better implementation. Based on such an understanding, the technical solution of the present invention essentially or part that contributes to the existing technology can be embodied in the form of a software product, which is stored in a storage medium (such as ROM/RAM, magnetic disk, optical disc) and includes several instructions for causing a terminal device (which may be a mobile phone, a computer, a server, or a network device, etc.) to execute the methods described in the embodiments of the present invention.

An embodiment of the present invention also provides a lift-off type laser tooth preparation apparatus, which may implement the preferred embodiments and exemplary embodiments above, the details of which are therefore omitted. As used below, the terms "module", "unit" or "subunit" may be used to describe software and/or hardware that can achieve a predetermined function. Although the devices described in the following embodiments are preferably implemented in software, hardware or a combination of software and hardware may also be possible and conceivable.

FIG. 25 is a structural block diagram of a lift-off type laser tooth preparation apparatus. As shown in FIG. 25, the apparatus includes:

an acquisition module 251, configured to acquire a first STL model of a target tooth and a second STL model of a tooth preparation for the target tooth;

a first generation module 252, configured to generate an STL model of a lifted-off surface that has an inverted-cone shape where the cone has a generatrix at a predetermined angle with respect to its axis, and has a base that is a three-dimensional contour of an outer edge of a shoulder of the second STL model;

a second generation module 253, configured to perform a Boolean operation between the STL model of the lifted-off surface and the first STL model, to obtain a third STL model;

a third generation module 254, configured to perform a Boolean operation between the second STL model and the third STL model, to obtain a fourth STL model that is to be removed;

a fourth generation module 255, configured to generate a multi-layer laser cutting path according to the fourth STL model, so as to control a laser tooth preparation device to perform tooth preparation on the target tooth according to the multi-layer laser cutting path.

It should be noted that each of the foregoing modules may be implemented by software or hardware. For the latter, the modules may be implemented in the following manner, but is not limited thereto: the modules are all located in the same processor; or the above modules are located in multiple different processors respectively.

In addition, the lift-off type laser tooth preparation method according to an embodiment of the present invention described with reference to FIG. 2 may be implemented by a lift-off type laser tooth preparation device. FIG. 26 is a schematic diagram illustrating a hardware structure of a lift-off type laser tooth preparation device.

The lift-off type laser tooth preparation device may include a processor 261 and a memory 262 storing computer program instructions.

Specifically, the foregoing processor 261 may include a central processing unit (CPU), or an application specific integrated circuit (ASIC), or may be one or more integrated circuits that implement an embodiment of the present invention.

The memory 262 may be a mass storage for data or instructions. By way of example, and not limitation, the memory 262 may be a hard disk drive (HDD), floppy disk drive, flash memory, optical disc, magneto-optical drive, magnetic tape or universal serial bus (USB) drive, or a combination of two or more of these. Where appropriate, the memory 262 may be removable or non-removable (or fixed) media. Where appropriate, the memory 262 may be internal or external to the data processing device. In a particular embodiment, the memory 262 is a non-volatile solid-state memory. In a particular embodiment, the memory 262 is a read-only memory (ROM). Where appropriate, the ROM can be a Mask ROM (MROM), a programmable ROM (PROM), an erasable PROM (EPROM), an electrically erasable PROM (EEPROM), an electrically rewritable ROM (EAROM) or a flash memory or a combination of two or more of these.

The processor 261 reads and executes the computer program instructions stored in the memory 262 to implement any one of the lift-off type laser tooth preparation methods in the above embodiments.

In one example, the lift-off type laser tooth preparation device may further include a communication interface 263 and a bus 260. As shown in FIG. 26, the processor 261, the memory 262 and a communication interface 263 are connected through the bus 260 and communicate with one another.

The communication interface 263 is mainly used to implement communication between various modules, apparatus, units, and/or devices in the embodiments of the present invention.

The bus 260 may include hardware, software, or both, to couple the components of the lift-off type laser tooth preparation device together. By way of example and not limitation, the bus may include an accelerated graphics port (AGP) or other graphics bus, an enhanced industry standard architecture (EISA) bus, a front side bus (FSB), a super transfer (HT) interconnect, an industry standard architecture (ISA) Bus, Infinite Bandwidth Interconnect, Low Pin Count (LPC) Bus, Memory Bus, Micro Channel Architecture (MCA) Bus, Peripheral Component Interconnect (PCI) Bus, PCI-Express (PCI-X) Bus, Serial Advanced Technology Attachment (SATA) bus, Video Electronics Standards Association Local (VLB) bus or other suitable bus or a combination of two or more of these. Where appropriate, the bus 260 may include one or more buses. Although the embodiments of the present invention describe and illustrate a particular bus, the present invention does not concern any suitable bus or interconnect.

Based on acquired data, the lift-off type laser tooth preparation device can execute the lift-off type laser tooth preparation method of the embodiment of the present invention, thereby implementing the lift-off type laser tooth preparation method described in conjunction with FIG. 2.

In addition, the lift-off type laser tooth preparation methods in the foregoing embodiments may be implemented with a computer-readable storage medium. A computer program instruction is stored on the computer-readable storage medium, and when the computer program instruction is executed by a processor, any one of the lift-off type laser tooth preparation methods in the foregoing embodiments can be implemented.

The above descriptions are merely preferred embodiments of the present invention, and are not intended to limit the present invention. For those skilled in the art, the present invention may have various modifications and changes. Any modification, equivalent replacement or improvement made within the spirit and principle of the present invention shall fall within the scope of protection of the present invention.

INDUSTRIAL APPLICABILITY

The method, apparatus, device and medium of lift-off type laser tooth preparation provided by the embodiments of the present invention solve the problem of layer-by-layer laser tooth preparation that layer-by-layer laser tooth preparation is low in efficiency, and improve the efficiency of tooth preparation for molar teeth that are large in size.

The invention claimed is:

1. A lift-off type laser tooth preparing method, comprising:
   acquiring a first STL model of a target tooth and a second STL model of a tooth preparation for the target tooth;
   generating an STL model of a lifted-off surface that has an inverted-cone shape where the cone has a generatrix at a predetermined angle with respect to its axis, and has a base that is a three-dimensional contour of an outer edge of a shoulder of the second STL model;
   performing a Boolean operation between the STL model of the lifted-off surface and the first STL model, to obtain a third STL model;
   performing a Boolean operation between the second STL model and the third STL model, to obtain a fourth STL model that is to be removed;
   generating a multi-layer laser cutting path according to the fourth STL model; and
   controllinq a laser tooth preparing device to perform tooth preparing process on the target tooth according to the multi-layer laser cutting path.

2. The method according to claim 1, wherein, prior to the acquiring a first STL model of a target tooth and a second STL model of a tooth preparation for the target tooth, the method further comprises:
   acquiring three-dimensional surface data of the target tooth by using a three-dimensional intra-oral scanner, and storing the data as the first STL model; and
   designing based on the first STL model according to clinical requirements to obtain the second STL model.

3. A non-transitory computer-readable storage medium, storing a computer program instruction, wherein when executed by a processor, the computer program instruction implements the method of claim 2.

4. The method according to claim 1, wherein the predetermined angle ranges from 3° to 10°.

5. A non-transitory computer-readable storage medium, storing a computer program instruction, wherein when executed by a processor, the computer program instruction implements the method of claim 4.

6. The method according to claim 1, wherein the generating a multi-layer laser cutting path according to the fourth STL model comprises:
   slicing the fourth STL model into layers and generating a cross-sectional contour for each layer;
   for each layer filling the cross-sectional contour with parallel fill lines at a predetermined interval, and extracting a laser cutting path for each layer.

7. A non-transitory computer-readable storage medium, storing a computer program instruction, wherein when executed by a processor, the computer program instruction implements the method of claim 6.

8. A non-transitory computer-readable storage medium, storing a computer program instruction, wherein when executed by a processor, the computer program instruction implements the method of claim 1.

9. A lift-off type laser tooth preparing system, comprising a laser tooth preparation device, at least one processor, and at least one memory storing program codes, wherein the processor performs the stored program codes for:
   acquiring a first STL model of a target tooth and a second STL model of a tooth preparation for the target tooth;
   generating an STL model of a lifted-off surface that has an inverted-cone shape where the cone has a generatrix at a predetermined angle with respect to its axis, and has a base that is a three-dimensional contour of an outer edge of a shoulder of the second STL model;
   performing a Boolean operation between the STL model of the lifted-off surface and the first STL model, to obtain a third STL model;
   performing a Boolean operation between the second STL model and the third STL model, to obtain a fourth STL model that is to be removed;
   generating a multi-layer laser cutting path according to the fourth STL model; and
   controlling the laser tooth preparation device to perform tooth preparation on the target tooth according to the multi-layer laser cutting path.

10. A lift-off type laser tooth preparation system according to claim 9, wherein the processor performs the stored program codes further for:
    acquiring three-dimensional surface data of the target tooth by using a three-dimensional intra-oral scanner, and storing the data as the first STL model; and
    designing based on the first STL model according to clinical requirements to obtain the second STL model.

11. A lift-off type laser tooth preparation system according to claim 9, wherein the predetermined angle ranges from 3° to 10°.

12. A lift-off type laser tooth preparation system according to claim 9, wherein the processor performs the stored program codes further for:
    slicing the fourth STL model into layers and generating a cross-sectional contour for each layer; and
    for each layer filling the cross-sectional contour with parallel fill lines at a predetermined interval, and extracting a laser cutting path for each layer.

* * * * *